(12) United States Patent
Silvian

(10) Patent No.: US 6,400,990 B1
(45) Date of Patent: Jun. 4, 2002

(54) PATIENT ACTIVATED TELEMETRY CONTROL UNIT USING BIDIRECTIONAL ASYMMETRIC DUAL-MODE TELEMETRY LINK TO COMMUNICATE WITH AN IMPLANTED DEVICE

(75) Inventor: Sergiu Silvian, La Crescenta, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/507,171

(22) Filed: Feb. 18, 2000

(51) Int. Cl.⁷ .............................. A61N 1/02; H04B 5/00
(52) U.S. Cl. ............................. 607/60; 607/30; 607/31; 607/32
(58) Field of Search ............................. 607/30, 31, 32, 607/60, 27; 340/573.1; 128/903

(56) References Cited

U.S. PATENT DOCUMENTS

| | | | |
|---|---|---|---|
| 3,727,616 A | * 4/1973 | Lenzkes | |
| 4,625,730 A | 12/1986 | Fountain et al. | 128/419 D |
| 4,681,111 A | 7/1987 | Silvian | 128/419 PT |
| 4,847,617 A | 7/1989 | Silvian | 340/870 |
| 4,884,575 A | 12/1989 | Sanders | 128/419 PG |
| 4,940,052 A | 7/1990 | Mann et al. | 128/419 |
| 4,944,298 A | 7/1990 | Sholder | 128/419 |
| 4,944,299 A | * 7/1990 | Silvian | |
| 4,980,898 A | 12/1990 | Silvian | 375/59 |
| 5,058,581 A | 10/1991 | Silvian | 128/419 PG |
| 5,330,507 A | 7/1994 | Schwartz | 607/14 |
| 5,342,408 A | * 8/1994 | deCoriolis et al. | |
| 5,466,246 A | * 11/1995 | Silvian | |
| 5,490,862 A | 2/1996 | Adams et al. | 607/6 |
| 5,562,713 A | 10/1996 | Silvian | 607/32 |
| 5,630,836 A | * 5/1997 | Prem et al. | |
| 5,752,976 A | 5/1998 | Duffin et al. | 607/32 |
| 5,755,737 A | 5/1998 | Prieve et al. | 607/4 |
| 5,769,876 A | 6/1998 | Silvian | 607/60 |
| 5,876,353 A | 3/1999 | Riff | 600/547 |
| 5,899,931 A | * 5/1999 | Deschamp et al. | |
| 5,978,713 A | * 11/1999 | Prutchi et al. | |
| 6,106,551 A | * 8/2000 | Crossett et al. | |
| 6,200,265 B1 | * 3/2001 | Walsh et al. | |
| 6,263,245 B1 | * 7/2001 | Snell | |

* cited by examiner

*Primary Examiner*—Kennedy Schaetzle

(57) ABSTRACT

A dual-mode telemetry system that allows digital binary data to be efficiently transferred between an implantable device and a patient control unit. The patient control unit utilizes a bidirectional, asymmetric, telemetry link, wherein in a first mode, the patient control unit transmits data at a high bit rate to the implanted device, and in a second mode, the patient control unit receives data at a low bit rate from the implanted device. The telemetry system is relatively simple and inexpensive to construct, and requires minimal modifications to the implanted device.

30 Claims, 6 Drawing Sheets

8 KBS PCU TO IMPLANT

OUTPUT FROM IMPLANT TO PCU

INPUT TO A/D OF PCU

PATIENT ACTIVATED TELEMETRY CONTROL UNIT USING BIDIRECTIONAL ASYMMETRIC DUAL-MODE TELEMETRY LINK TO COMMUNICATE WITH AN IMPLANTED DEVICE

FIELD OF THE INVENTION

The present invention relates generally to cardiac pacing devices and other types of implantable medical devices that can be programmed and/or analyzed following implantation using an external diagnostic/programmer system. Particularly, this invention relates to a patient activated telemetry control unit that uses a bidirectional link to communicate with implantable devices. More specifically, the patient control unit utilizes a bidirectional, asymmetric, dual-mode telemetry link, wherein in the first mode, the patient control unit transmits data at a high bit rate to the implanted device, and in the second mode, the patient control unit receives data at a low bit rate from the implanted device.

BACKGROUND OF THE INVENTION

Implantable devices are implanted in a human or animal for the purpose of performing a desired function. This function may be purely observational or experimental in nature, such as monitoring certain body functions; or it may be therapeutic or regulatory in nature, such as providing critical electrical stimulation pulses to certain body tissue, nerves or organs for the purpose of causing a desired response. Implantable medical devices such as pacemakers, perform both observational and regulatory functions, i.e., they monitor the heart to ensure it beats at appropriate intervals; and if not, they cause an electrical stimulation pulse to be delivered to the heart in an attempt to force the heart to beat at an appropriate rate.

In order for an implantable device to perform its functions at minimum inconvenience and risk to the person or animal within whom it is used, a noninvasive telemetry means has been provided to allow data and commands to be easily passed back and forth between the implantable device and an external device. Such an external device, known by a variety of names, such as a controller, programmer, or monitor, provides a convenient mechanism through which the operation of the implantable device can be controlled and monitored, and through which data sensed or detected by the implantable device can be transferred out of the implantable device to an external (non-implanted) location where it can be read, interpreted, or otherwise used in a constructive manner.

As the sophistication of implantable devices has increased in recent years, emphasis on the amount of data that must be transferred between an implantable device and its accompanying external device or programmer, has dramatically increased. This, in turn, has resulted in a search for more efficient ways to effectuate such a data transfer at high speed. Such high speed data transfer typically increases the complexity and cost of the telemetry system, thus rendering the use of an additional patient controlled telemetry system an inefficient and impractical proposition.

Another challenge facing the implementation of a practical patient controlled telemetry system is the complexity and relatively high cost and large size of a patient controlled telemetry system that communicates with the implanted device.

While certain devices incorporate patient activation features by allowing the patients to provide input to the telemetry system, they add design complexity and cost. Some of these exemplary devices are described in the following patents.

U.S. Pat. No. 4,625,730 to Fountain et al., entitled "Patient ECG Recording Control for an Automatic Implantable Defibrillation" describes an implantable automatic defibrillator includes sensors which are placed on or near the patient's heart to detect electrical signals indicative of the physiology of the heart. The signals are digitally converted and stored into a FIFO region of a RAM by operation of a direct memory access (DMA) controller. The DMA controller operates transparently with respect to the microprocessor which is part of the defibrillator. The implantable defibrillator includes a telemetry communications circuit for sending data outbound from the defibrillator to an external device (either a patient controller or a physician's console or other) and a receiver for sensing at least an externally generated patient ECG recording command signal. The patient recording command signal is generated by the hand held patient controller. Upon detection of the patient ECG recording command, DMA copies the contents of the FIFO into a specific region of the RAM.

U.S. Pat. No. 4,884,575, entitled "Cardiac Pacer with Patient-Controlled Exercise Rate and Method" describes a cardiac pacemaker pulse generator adapted to generate electrical stimuli at a first pacing rate, and to selectively increase the rate to a second higher pacing rate. A timer triggers the rate increase to establish the higher rate as an exercise rate following the passage of a preset period of time after the timer is enabled. An external magnet controlled by the patient activates a reed switch to enable the timer to commence timing. The pulse generator is further adapted to respond to a second pass of the magnet over the reed switch after enabling of the timer to thereupon disable the timer before the preset period of time has expired. If the second pass of the magnet occurs after the exercise rate has begun, the element for increasing the rate is disabled to return the pulse generator to the lower pacing rate.

U.S. Pat. No. 5,490,862, entitled "Atrial Defibrillator Having Patient Activated Modality" describes an implantable atrial defibrillator that includes a programming means responsive to a patient activated mode command, for causing the sequence initiating means to activate an intervention sequence means only in response to a sequence command, and an automatic mode command for causing the sequence initiating means to activate the intervention sequence means at predetermined times. The programming means is responsive to the patient activated mode command for causing the sequence initiating means to activate the intervention sequence means only in response to the sequence command generated from external to the patient and responsive to a combined automatic and patient activated mode command for causing the sequence initiating means to activate the intervention sequence means in response to the sequence command at predetermined times.

U.S. Pat. No. 5,752,976, titled "World wide Patient Location and Data Telemetry System for Implantable Medical Devices" describes a method for communicating with an implanted medical device. The medical device includes a telemetry transceiver for communicating data and operating instructions between the implanted device and an external patient communications control device that is located in proximity to the patient within the implanted device transceiving range. The control device includes a patient activated link for permitting patient initiated personal communication with the medical support network. A system controller in the control device controls data and voice communications for selectively transmitting patient initiated personal communications and global positioning data to a medical support network.

U.S. Pat. No. 5,755,737, entitled "Method and Apparatus for Diagnosis and Treatment of Arrhythmias" describes an implantable anti-arrhythmia device with an associated patient activator. The patient is provided with an activator which informs the implanted device that the patient believes that anti-arrhythmia therapy is necessary. In response to receipt of the activation signal, the implanted device defines a time interval thereafter during which a second, less stringent set of arrhythmia detection criteria must be met, in response to which the device will deliver a cardioversion or defibrillation pulse.

SUMMARY OF THE INVENTION

One feature of the present invention is to satisfy the still unsatisfied need to improve the patient's control of an implanted medical device and thus physiological condition, by providing the patient with a control unit which is small in size, relatively inexpensive, and simple to produce and to use. The patient activated telemetry control unit can be designed and implemented with minimal design changes to existing telemetry systems, and without significantly increasing the overall cost of the implanted device.

The patient control unit uses a bidirectional, asymmetric, dual-mode telemetry link, to communicate with the implantable device. In a first mode, the patient control unit transmits data at a high bit rate to the implanted device, and in the second mode, the patient control unit receives data at a low bit rate from the implanted device.

While in the second or receive mode, the patient activated telemetry control unit receives data at a low speed using a particular mode of operation of the implanted device. According to this mode of operation, each byte transmitted to the patient activated telemetry control unit is comprised of a predetermined number of identical bits, i.e., eight ones or eight zeros. The patient activated telemetry control unit recognizes each of the received bytes as a single bit, and the reception rate is therefore reduced to, for example, one eight. As a result of such a reduction in the reception bit rate, the hardware design and implementation of the patient activated telemetry control unit are greatly simplified and its cost reduced to within practical and affordable limits.

DESCRIPTION OF THE DRAWINGS

The various features of the present invention and the manner of attaining them will be described in greater detail with reference to the following description, claims, and drawings, wherein reference numerals are reused, where appropriate, to indicate a correspondence between the referenced items, and wherein:

DETAILED DESCRIPTION OF THE INVENTION

Figure 1:
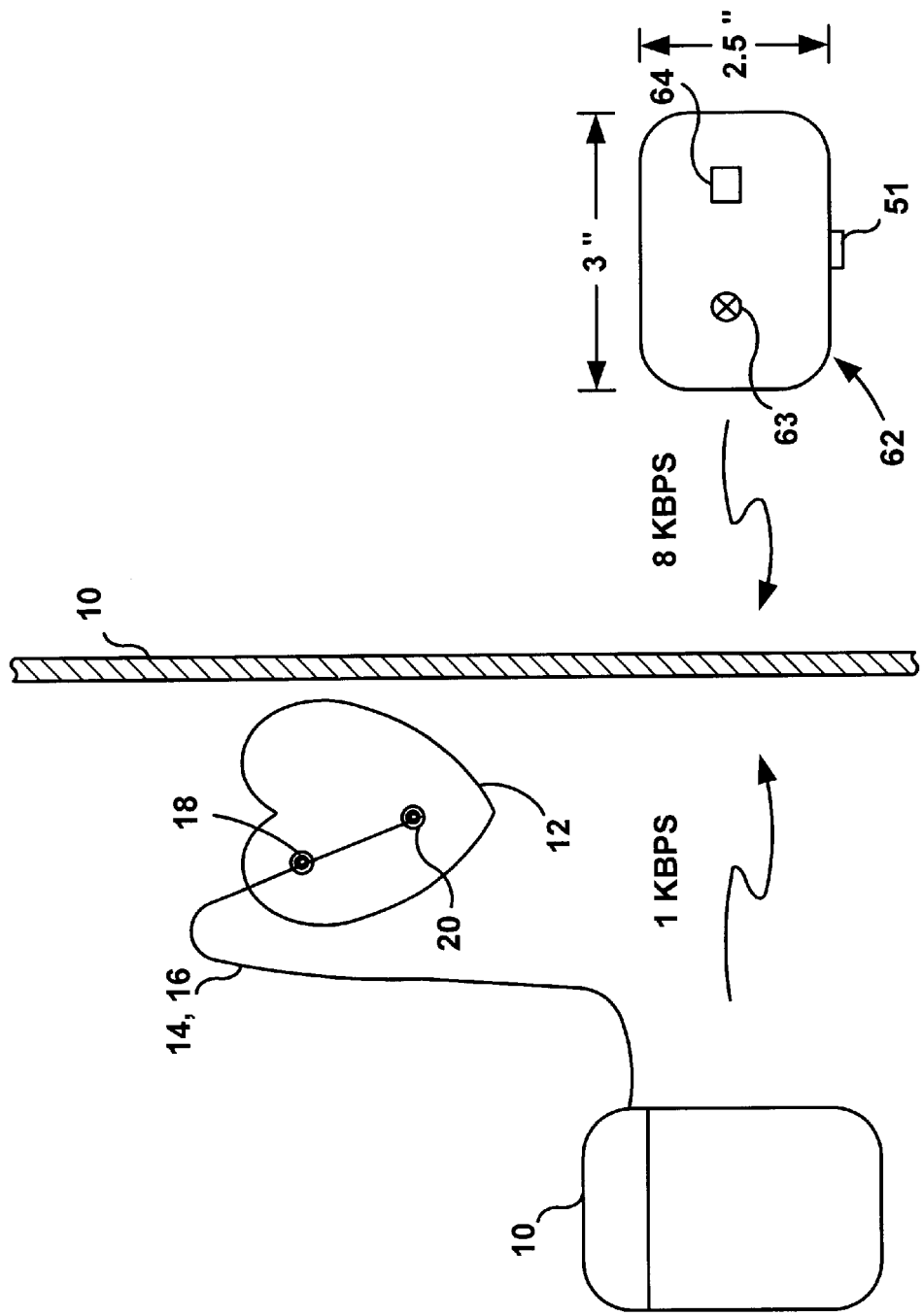
FIG. 1 is a schematic view of an implantable stimulation device shown in telemetric communication with a patient activated telemetry control unit according to the present invention.
Figure 2:
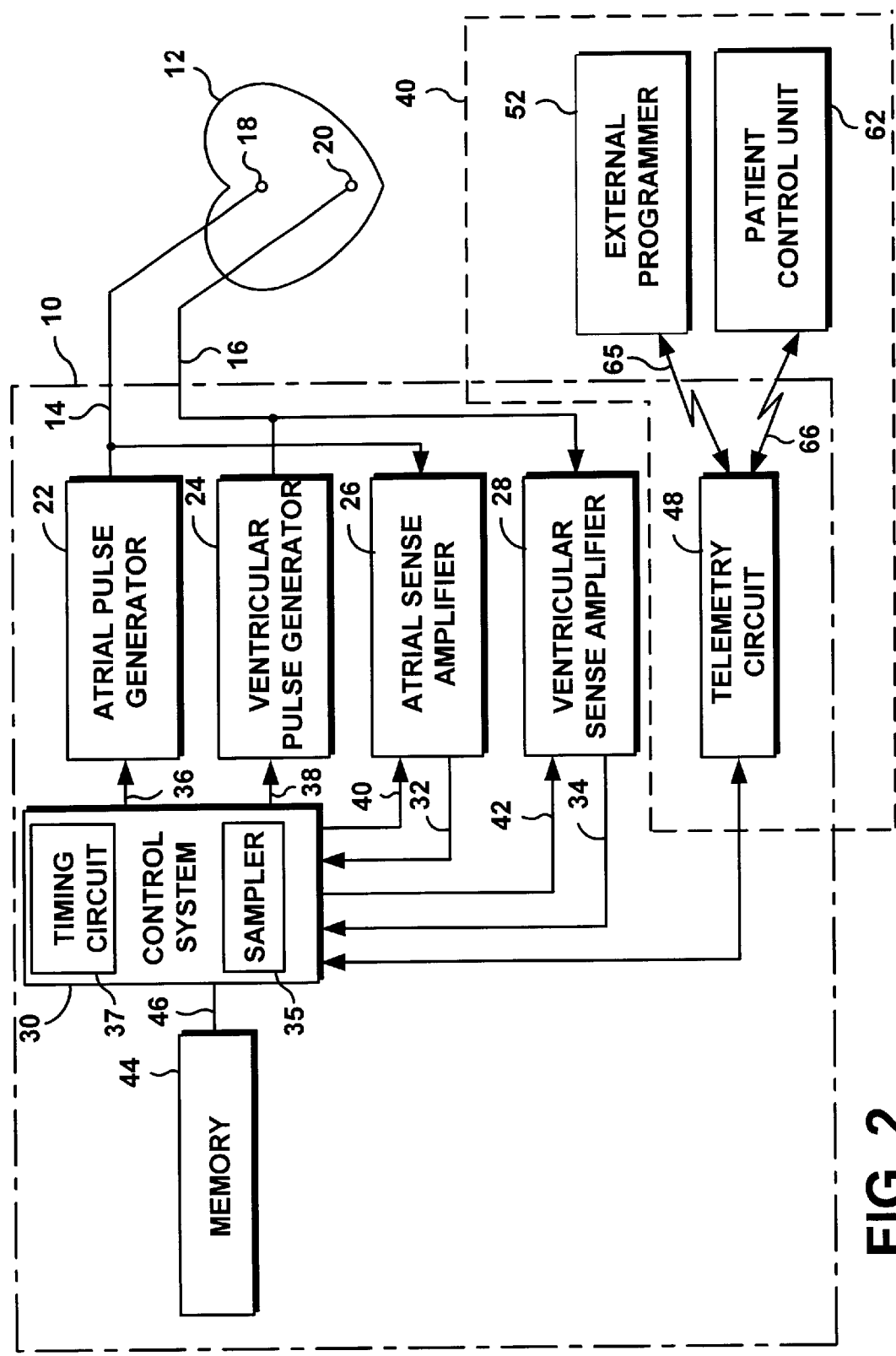
FIG. 2 is a functional block diagram of an implantable dual-chamber pacemaker, which represents an exemplary type of implantable medical devices with which the invention may be used.

With reference to FIGS. 1 and 2, the system and method of the present invention are intended for use in an implantable cardiac stimulation device 10, such as a pacemaker, a defibrillator, a cardioverter, an implantable cardioverter-defibrillators ("ICDs"), or a similar stimulation device capable of monitoring and detecting electrical activities and events within a patient's organ such as a heart 12. For illustration purposes, the cardiac stimulation device will be referred to herein as pacemaker 10.

The pacemaker 10 is coupled to a patient's heart 12 by way of leads 14 and 16, and is implanted beneath a layer or skin 17 of a patient or animal. The lead 14 includes an electrode 18 which is in contact with one of the atria of the heart 12. The lead 16 includes an electrode 20 which is in contact with one of the ventricles. The lead 14 carries stimulating pulses to the electrode 18 from an atrial pulse generator 22, while the lead 16 carries stimulating pulses to the electrode 20 from a ventricular pulse generator 24. In addition, electrical signals from the atria are carried from the electrode 18, through the lead 14, to the input terminal of an atrial sense amplifier 26. Electrical signals from the ventricles are carried from the electrode 20, through the lead 16, to the input terminal of a ventricular sense amplifier 28.

Operatively controlling the dual-chamber pacemaker 10 is a control system 30. The control system 30 is preferably a microprocessor-based system such for example as that disclosed in commonly assigned U.S. Pat. No. 4,940,052 of Mann, which is incorporated herein by reference in its entirety. The control system 30 may also be a state logic-based system such for example as that disclosed in commonly assigned U.S. Pat. No. 4,944,298 of Sholder, which is also incorporated herein by reference in its entirety.

The control system 30 includes a timing circuit 37 comprised of a real-time clock, for providing timing functionality for monitoring cardiac events and for timing the application of therapeutic pulses by the pulse generators 22 and 24. The control system 30 also includes a sampler 35, such as an A/D converter, for generating digital signals representative of cardiac activity, by sampling the atrial and/or ventricular cardiac signals acquired by the respective amplifiers 26 and 28. Alternately, the sampler 35 may be implemented separately from the control system 30 and connected directly to the amplifiers 26 and 28.

The pacemaker 10 also includes a memory 44 which is coupled to the control system 30. The memory 44 allows certain control parameters used by the control system 30 in controlling the operation of the pacemaker 10 to be programmably stored and modified, as required, to customize the operation of the pacemaker 10 to suit the needs of a particular patient. In particular, parameters regulating the operation of the sampler 35 are stored in the memory 44. In addition, samples acquired by the sampler 35 may be stored in the memory 44 for later analysis by the control system 30.

The control system 30 receives the output signals from the atrial sense amplifier 26. Similarly, the control system 30 also receives the output signals from the ventricular sense amplifier 28. These various output signals are generated each time that an atrial event (e.g. a P-wave) or a ventricular event (e.g. an R-wave, far-field R-wave (FFR), or a far-field T-wave (FFT) is sensed within the heart 12.

The control system 30 also generates an atrial trigger signal that is sent to the atrial pulse generator 22, and a ventricular trigger signal that is sent to the ventricular pulse generator 24. These trigger signals are generated each time that a stimulation pulse is to be generated by one of the pulse generators 22 or 24. The atrial stimulation pulse is referred to as the "A-pulse", and the ventricular stimulation pulse is referred to as the "V-pulse". The characteristics of these stimulation pulses are determined by pacing energy settings that are among the parameters stored in the memory 44. The control system 30 may also be programmed to operate the pacemaker 10 in a variety of pacing and sensing modes.

The operation of the pacemaker 10 is generally controlled by a control program stored in the memory 44 and executed by the control system 30. This control program is typically comprised of multiple integrated program modules, with each module bearing responsibility for controlling one or more functions of the pacemaker 10. For example, one program module may control the delivery of stimulating pulses to the heart 12, while another may control the verification of ventricular capture and ventricular pacing energy determination. In effect, each program module is a control program dedicated to a specific function or set of functions of the pacemaker 10.

Figure 3:
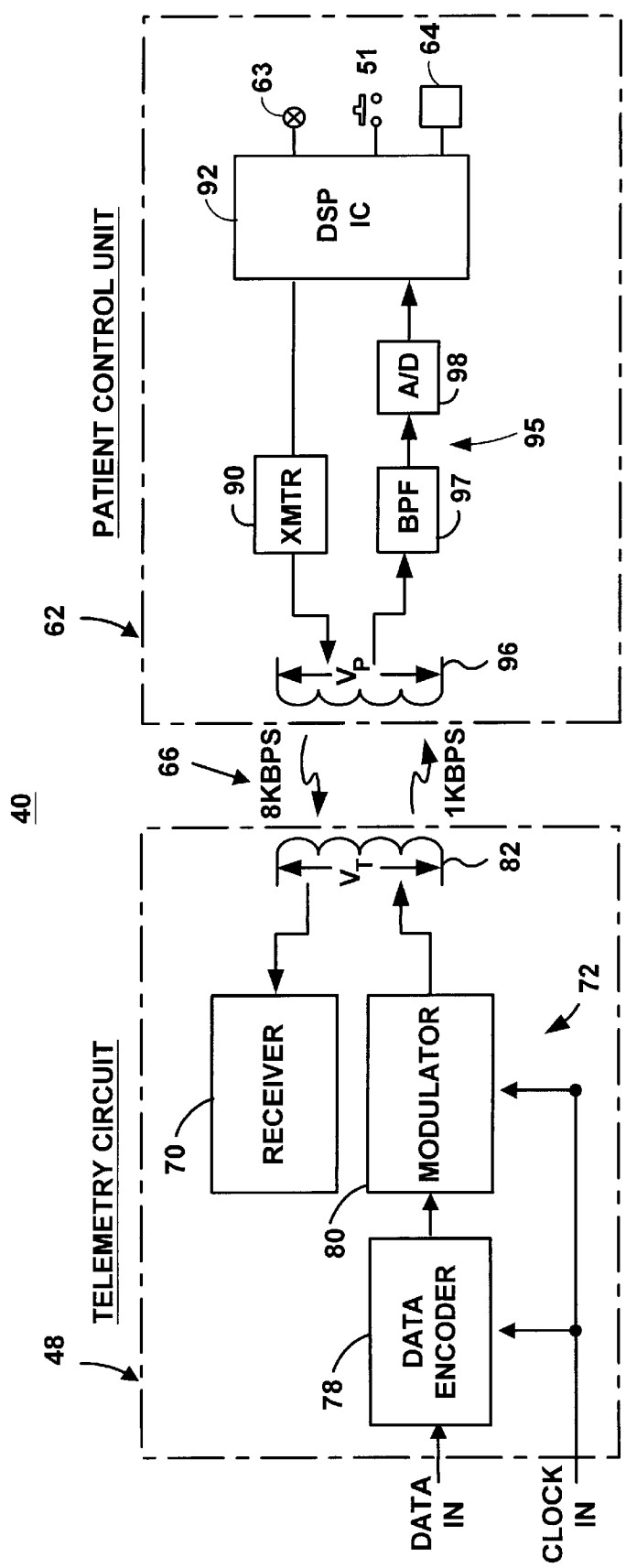
FIG. 3 is a high level schematic diagram of a telemetry system of the present invention comprised of a transceiving unit forming part of the stimulation device of FIG. 1, and a patient control unit.

FIGS. 2 and 3 illustrate a telemetry system 40 according to the present invention. The telemetry system 40 is comprised of the telemetry circuit 48 which is contained within the pacemaker 10 and which coupled to the control system 30, and a patient activated telemetry control unit (PCU) 62. The patient control unit 62 is relatively small in size. According to an exemplary implementation, the patient control unit 62 has a length of approximately 3 inches and a width of approximately 2.5 inches. It should be clear that the patient control unit 62 is not drawn to scale, and that other dimensions are possible.

With reference to FIG. 1, the patient control unit 62 is simple to use. According to one particular embodiment, the patient control unit 62 includes a push-button switch 51 that activates the patient control unit 62 and that sends commands to the pacemaker 10. The patient control unit 62 also includes an input element 64 that enables the patient to select and input the desired command type. In one embodiment, the input element 64 can be a two-position slide switch (e.g. with a command 1 position and a command 2 position) that enables the patient to enter instructions for communication to the pacemaker 10. It should be clear that the input element 64 can alternatively be a more complex device such as a keypad, a pointing device, an audio input device such as a microphone, and so forth. An exemplary command that can be inputted by the patient includes but is not limited to instructing the pacemaker 10 to start recording an event when, for instance, the patient feels weak, or feels his or her heart rate accelerating.

In addition, the patient control unit 62 includes a display 63 that provides the patient with a confirmation response from the pacemaker 10. The display 63 is interchangeably referred to herein as status indicator 63, and can be, for example, a simple LED that can flash at a given rate or be lit continuously after a command is recognized by the pacemaker 10. Alternatively, the display 63 can be a more complicated display such as a liquid crystal display (LCD), or any other audio or visual device.

With reference to FIG. 2, the telemetry circuit 48 of the pacemaker 10 and the patient control unit 62 may be coupled over a communication link 66. The telemetry circuit 48 may also be coupled to an external programmer 52 over a communication link 65. Optionally, a bidirectional, asymmetric, dual-mode telemetry link (similar to the link 66) can be established between the patient control unit 62 and the external programmer 52, to enable a remotely located physician to interrogate the patient control unit 62 via the external programmer 52, and also to allow the patient to interrogate the external programmer 52 via the patient control unit 62. The communication links, i.e., 65, 66 can include an electromagnetic telemetry link or a remote communication link such as a pair of modems interconnected by way of a telecommunications link and equipped with telemetry capabilities.

The telemetry operation between the telemetry circuit 48 and the external programmer 52 is described, for example, in U.S. Pat. No. 4,944,299 to Silvian and U.S. Pat. No. 4,980,898 to Silvian, that are incorporated herein by reference, and therefore it will not be described herein a detail.

FIG. 3 illustrates the implanted telemetry circuit 48 in communication with the patient control unit 62 by way of the telemetry link 66. The telemetry circuit 48 includes a receiver 70 and a transmitter 72. The receiver 70 communicates data with the patient control unit 62 over a coil 82. The transmitter 72 is generally comprised of a data encoder 78 and a modulator 80. Input data (DATA IN) is fed to the transmitter 72 where it is encoded by the encoder 78, modulated by the modulator 80, and transmitted by the coil 82 to the patient control unit 62. A clock signal (CLOCK IN) controls the clock signals to the telemetry circuit 48.

An important aspect of the present invention is that the patient control unit 62 uses a bidirectional, asymmetric, dual-mode telemetry link, to communicate with the telemetry circuit 48. In a first mode, the patient control unit 62 transmits data at a high or normal bit rate (e.g. 8192 Hz or 8 Kbps) to the pacemaker, and in a second mode, it receives data at a low bit rate (e.g. 1 Kbps) from the transmitter 80.

To this end, the patient control unit 62 includes a transmitter 90 that uses an intelligent controller 92, to transmit data according to the command selected by the input element 64, by way of a coil 96. In one embodiment, the DSP chip U2 is relatively inexpensive, and is available from Analog Devices Corporation as part number ADSP2104.

The patient control unit 62 further includes a receiver 95 which is comprised of a narrow band-pass filter 97 that receives data from the transmitter 72, by way of the coil 96, to reduce noise and to amplify the received signal. The filtered signals are then passed through an analogue to digital converter 98 to digitize the signals before they are processed by the controller 92. After processing, the controller 92 selectively activates the display 63.

When the patient wishes to interface with the pacemaker 10, the patient starts by selecting a desired command to be implemented by the pacemaker 10, by means of the input element 64. The patient then positions the patient control unit 62 in proximity to the telemetry circuit 48, and presses the switch 51. In one embodiment, the patient positions the patient control unit 62 as close as possible to the pacemaker 10 (e.g., within a few inches) so that the coil 96 of the patient control unit 62 is located in proximity to the coil 82 of the telemetry circuit 48.

Figure 4:
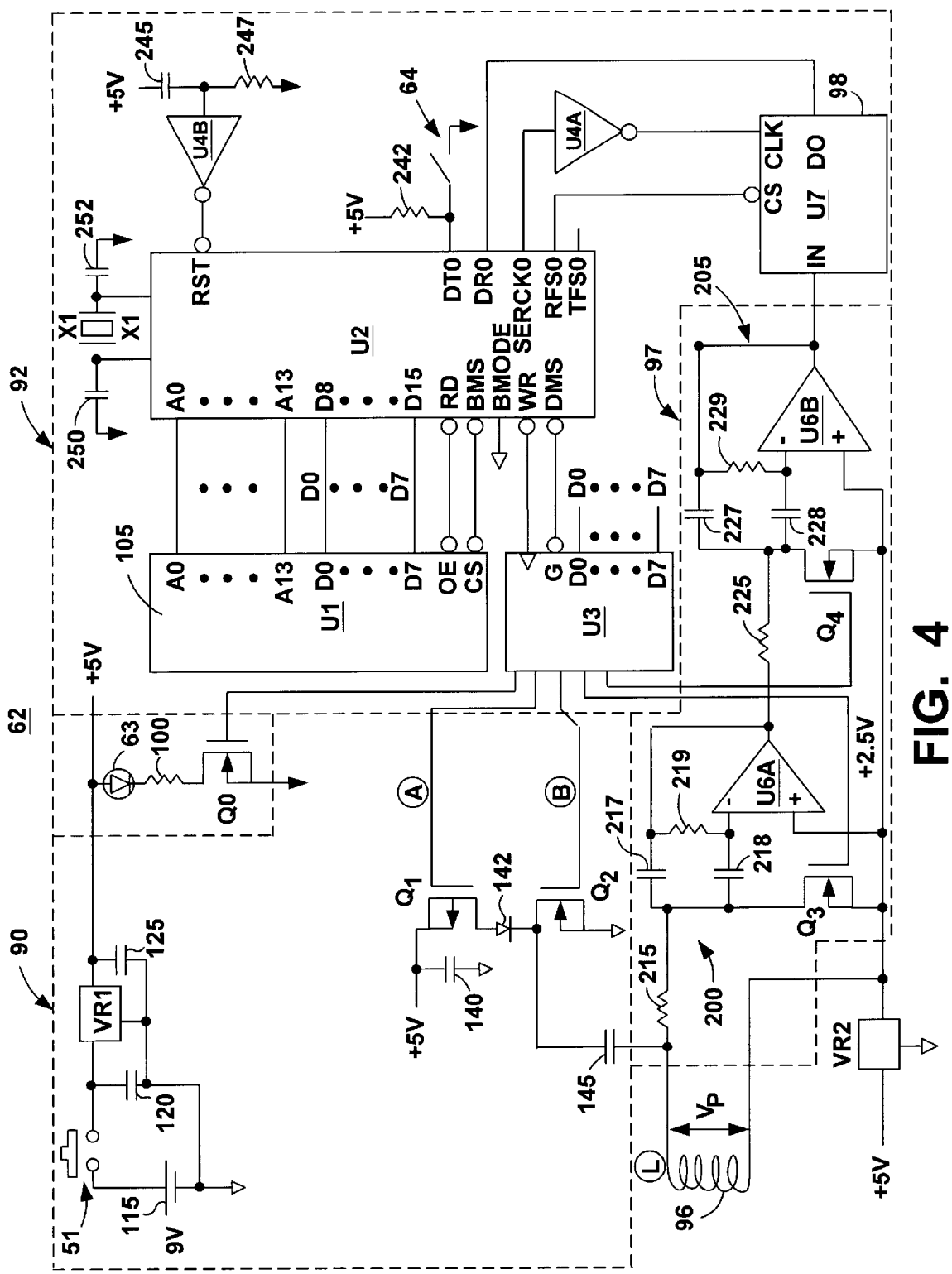
FIG. 4 is a more detailed circuit diagram of the patient control unit of FIG. 3, according to a first embodiment of the present invention.

The switch 51 connects the power source (battery) to the patient control unit 62 so that the controller chips 92 starts executing an executable program stored in memory 105 (FIG. 4). While in this embodiment the memory 105 is exemplified by an EPROM chip U1, it should be clear that alternative program storage devices can be used, and the DSP IC U2 can execute the program directly from the memory 105. Alternatively, the program can be loaded first by the DSP chip U2 in the DSP chip's U2 internal memory space where it is executed.

The patient control unit 62 sends the desired command to the implanted pacemaker 10, receives a response from the pacemaker 10, and displays the result to the patient. These operational steps are executed in approximately 50 ms to 100 ms, so that the patient watching the display 63 stops pressing the switch 51, thus de-energizing the patient control unit 62.

Figure 5:
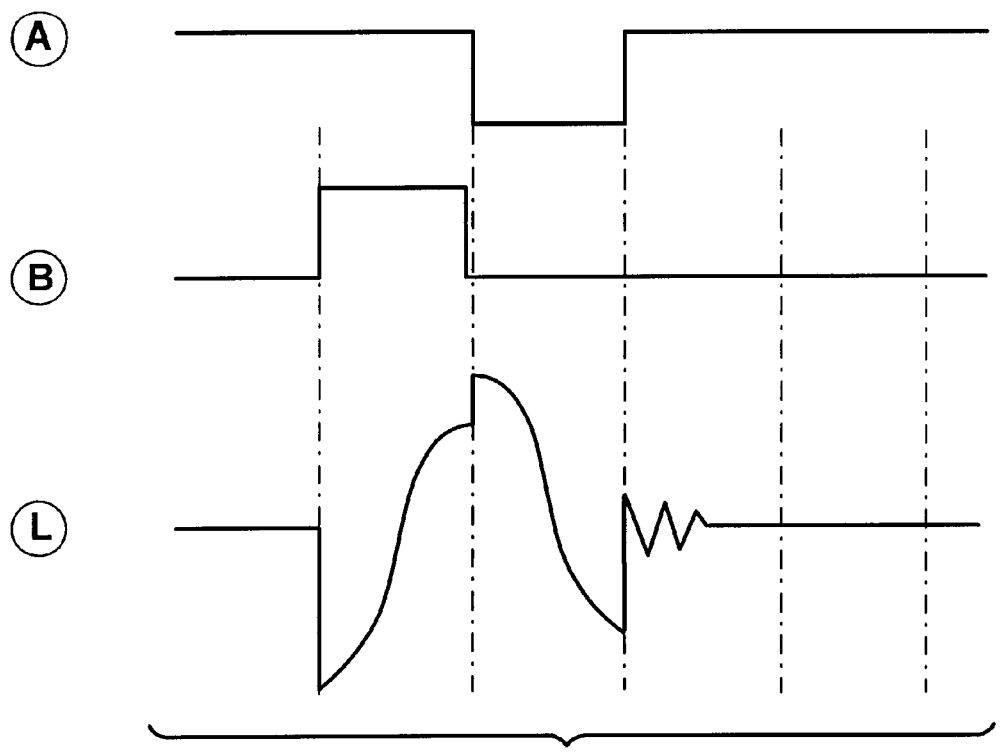
FIG. 5 is a waveform timing diagram that illustrates representative signal waveforms associated with a transmitter that forms part of the patient control unit of FIG. 4.

The two coils 82, 96 are thus inductively coupled to each other, and as such, a voltage signal $V_T$ appearing across the coil 82 is induced in the coil 96, where it appears as a voltage signal $V_P$ which is also designated by signal "L" (FIG. 5). Similarly, a voltage signal $V_P$ appearing across the coil 96 is induced in the coil 82, where it appears as a voltage signal $V_T$. The two coils 82, 96 thus function much the same as an air coil transformer, with the voltage applied to the one coil is transferred to the other coil as a function of the coupling coefficient between the two coils 82, 96, which coupling coefficient is highly dependent upon the separation distance between the two coils and the medium separating the two coils 82, 96. In one embodiment, the coil 96 has an inductance of approximately 300 μH.

The patient simply views the status indicator 63, which, after receiving a response from the pacemaker 10, is lit to provide an indication that the pacemaker 10 is operating properly and that the patient's command was executed by the pacemaker 10. In the embodiment of FIG. 4, the status indicator 63 is exemplified by a light emitting diode (LED), where a steady light indicates a proper functioning of the patient control unit 62, while a flashing light indicates that the patient's command has not been properly executed and that the patient needs to reinput the command. A MOSFET transistor switch Q0 is connected to the LED or status indicator 63 by way of a resistor 100.

Having described the main components and the method of use of the patient control unit 62, and the environment in which it operates, the patient control unit 62 will now be described in more detail in connection with FIGS. 4–9.

Referring to FIG. 4, a schematic/block diagram of a preferred embodiment of a burst mode transmitter 90 made in accordance with the present invention is shown. FIG. 5 illustrates representative waveforms that may be used with the operation of the burst mode transmitter 90 of FIG. 4.

The transmitter 90 is powered by a power source 115, such as a 9-Volt battery, which is coupled across the power switch 51 by way of a capacitor 120. A voltage regulator VR1 is connected to the power switch 51 and is coupled across the capacitor 120 at one end, and is further coupled across a capacitor 125 at its other end. The power regulator circuit comprised of the voltage regulator VR1, the capacitor 120, and the capacitor 125 regulates the input voltage from the battery 115, and reduces the input voltage to a positive (e.g. +5 Volts).

The output of the power regulator circuit is fed to the display 63, and to the controller chip (DSP IC) 92 and to other components as described below. When the patient elects to activate the transmitter 90, such as for issuing an instruction to the pacemaker 10 to perform a desired function, the patient selects the command by means of the input element 64 and then presses the switch 51, which activates the controller 92.

When power is applied to a digital signal processing (DSP) chip U2 and a trigger inverter U4B of the controller 92, a "power on reset" circuit, comprised of a capacitor 245 and a resistor 247, generates a short reset signal. In one embodiment, the trigger inverter U4 is a 74HC14 Schmidt trigger inverter. The reset signal resets the DSP chip U2.

The DSP chip U2 starts by "booting" and transferring a software program stored in the memory 105 (EPROM U1) to an internal memory of the DSP chip U2. Next, the DSP chip U2 commences the execution of the software program by inspecting the state of the input element 64, and starts communicating with the telemetry circuit 48 of the pacemaker 10. The controller 92 then displays the communication result to the patient by means of the display 63.

If the DSP chip U2 does not have sufficient I/O lines, a latch U3 is provided and written over by the DSP chip U2 with corresponding controls. In an exemplary design, only 5 of 8 I/O lines of the DSP chip U2 are used.

In turn, the latch U3 of the controller 92 applies a signal designated "A" to a gate of a MOSFET transistor switch Q1. The latch U2 also applies a signal designated "B" to a gate of a MOSFET transistor switch Q2 gate. Signals "A" and "B" are generated with proper timing in order to produce a pseudo-sinewave voltage (L) on the coil 96, as shown in FIG. 5.

The source of the MOSFET transistor switch Q1 is connected to a capacitor 140, and to a +5V potential. The drain of the MOSFET transistor switch Q1 is coupled to the drain of the MOSFET transistor switch Q2 by way of a diode 142.

The junction between the cathode of the diode 142 and the drain of the MOSFET transistor switch Q2 is connected to the coil 96 through a capacitor 145. The capacitor 145 tunes the coil 96 to approximately 50 kHz. The source of the MOSFET transistor switch Q2 is connected to ground potential.

Though the transistor switches Q1 and Q2 are described in term of MOSFET transistors, it should be clear that the switch function can be realized with any suitable transistor or equivalent device. Similarly, any of numerous commercially available solid state switches can be used for these switches and other switches constituting the patient control unit 62.

The operation of switches Q1 and Q2 is controlled by logic signals obtained from the outputs of the latch U3. The latch U3 enables only one of the switches Q1 or Q2 to be turned ON at any given time, and further allows both switches Q1 and Q2 to be turned OFF at the same time. In this way, the latch U3 prevents the switches Q1 and Q2 to be ON at the same time.

It is thus seen that the burst mode transmitter 90 periodically transmits or generates bursts of a carrier signal at a prescribed rate, wherein each burst includes one period of the carrier signal. Further, the carrier signal starts and stops each burst at a peak value, and this peak value is advantageously stored and used as the starting voltage of the carrier signal at the commencement of the next burst. The diode 142 is provided to allow the voltage at its junction with the capacitor 145 to exceed +5V. The transmitter 90 thus provided is low in cost, efficient to operate, and reliable in performance.

In one embodiment, when the patient control unit 62 is operating in a first mode, it transmits data at a high or normal bit rate (i.e., 8 Kbps) to the pacemaker 10.

The remaining components of the patient control unit 62 will now be described with reference to FIGS. 4 and 6–8. As illustrated in FIG. 4, the patient control unit 62 includes a voltage regulator VR2 which is connected to an input voltage (e.g. +5 Volts) to reduce it to a positive reference potential (+2.5 Volts) for biasing two amplifiers U6A and U6B.

In one embodiment, the band-pass filter 97 includes two second order band-pass filter circuits 200, 205. At the receive mode transfer bit rate of 1024 bps, the overall bandwidth of the band-pass filter 95 may be as narrow as 2000 Hz. Using a narrow bandwidth provides a significant improvement in the noise and EMI immunity. In contrast, using a higher rate (as 8192 bps) would require a much larger bandwidth and require a better signal to ratio.

The filter circuit 200 includes a resistor 215 which is connected at one end to the coil 96, and at its other end to two capacitors 217, 218. A resistor 219 is connected at one of its ends to the capacitor 217 and to the output of an amplifier U6A. At its other end, the resistor 219 is connected to the capacitor 218 and to the inverting input of the amplifier U6A. The non-inverting input of the comparator amplifier U6A is connected to the reference potential +2.5V.

The drain of a MOSFET transistor switch Q3 is connected to capacitors 217, 218, and its source is connected to the reference potential +2.5V. The gate of the MOSFET transistor switch Q3 is connected to the latch U3. Typically, the signals received by the coil 96 are significantly lower than the signals transmitted via the coil 96, and the transistor switch Q3 prevents the saturation of the band-pass filter 97 during transmission. To this end, during transmission, the latch U3 drives the transistor switch Q3 ON, for effectively shorting the inputs of the high-Q filter circuit 200.

The filter circuit 205 includes a resistor 225 which is connected at one end to the output of the amplifier U6A, and at its other end to two capacitors 227, 228. A resistor 229 is connected at one of its ends to the capacitor 227 and to the output of a amplifier U6B. At its other end, the resistor 229 is connected to the capacitor 228 and to the inverting input of the amplifier U6B. The non-inverting input of the amplifier U6B is connected to the reference potential +2.5V.

The drain of a MOSFET transistor switch Q4 is connected to capacitors 227, 228, and its source is connected to the reference potential +2.5V. The gate of the MOFET transistor switch Q4 is connected to the latch U3. In order for the transistor switch Q3 to prevent the saturation of the band-pass filter 97 during transmission, the latch U3 drives the transistor switch Q4 ON, for effectively shorting the inputs of the high-Q filter circuit 205.

The latch U3 controls the operation of the MOSFET transistor switches Q3 and Q4. During transmission, the latch U3 turns ON both transistor switches Q3 and Q4 simultaneously, to short the filter circuits 200 and 205. When the transmission phase is complete, the latch U3 turns OFF the transistor switches Q3 and Q4 sequentially, in this order, to activate the filter circuits 200 and 205 sequentially.

The output of the amplifier U6B is connected to the input (IN) of the analogue to digital (A/D) converter 98 that digitizes the received signals. The A/D converter 98 is available from National Semiconductor as part No. ADC 8031.

Considering now the controller 92, it is comprised of the DSP chip U2 which is connected to the A/D converter 98 through an inverter U4A in order to invert the U2 clock.

The controller 92 is also connected to an inverted chip select CS input of the A/D converter 98, in order to signal the A/D converter 98 to start a new conversion.

The output of the inverter U4B is connected to a RST input of the controller 92, and its input is connected to an RC circuit. The RC circuit includes a capacitor 245 which is connected at one end to a reference potential (e.g. +5 Volts), and at its other end to the input of the inverter U4B, and also to ground potential via a resistor 247. One end of the input element 64 is connected to a reference potential +5V by means of a resistor 242, and is further connected to a DT0 input of the controller 92.

A crystal X1 is connected between two capacitors 250 and 252, which, in turn, are connected to ground potential. The crystal X1 works with an oscillator internal to the DSP chip U2, to generate a U2 clock signal. As described above, the DSP chip U2 is connected to the EPROM U1 to execute a program stored therein, and is also connected to the latch U3 that controls the switches Q1, Q2, Q3 and Q4.

Figure 6:
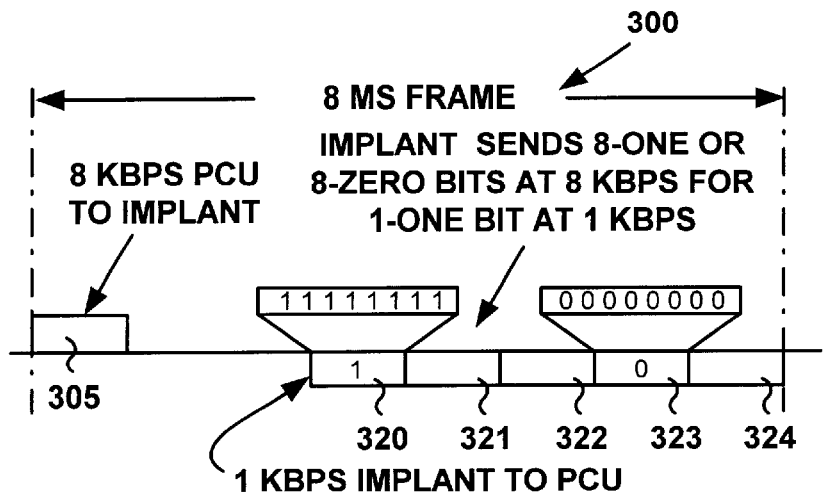
FIG. 6 depicts an 8 msec frame illustrating data communication bytes between the implantable device and the patient control unit of FIGS. 1 and 4.

With reference to FIG. 6, there is illustrated a frame 300, such as an 8-msec frame, that shows data communication between the pacemaker 10 and the patient control unit 62. The frame 300 includes a sequence of signals 305 (illustrated in more details in FIG. 9) representative of bits in a stream of data from the patient control unit 62 to the pacemaker 10 at a high bit rate, such as 8 Kbps. This rate is the same as the pacemaker 10 uses to communicate with the external programmer 52, and is relatively not complicated to generate by the patient control unit 62.

Figure 9:
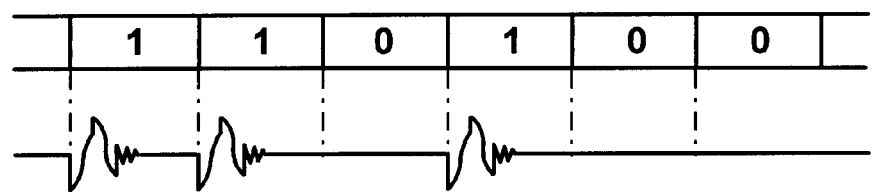
FIG. 9 depicts a sequence of signals and corresponding waveforms, representative of bits in a stream of data from the patient control unit of FIGS. 1 and 4 to the implantable device.

With reference to FIG. 9, when the patient control unit 62 sends a "1" bit to the pacemaker 10, it energizes the coil 96 with one cycle by controlling the signals "A" and "B".

This exemplary frame 300 also includes a string of five sequential bytes 320–324 that are transmitted from the pacemaker 10 to the receiver 95 of the patient control unit 62. An important feature of the present invention is that each of these exemplary bytes 320–324 includes identical bits, i.e., all 1's or all 0's, so that one byte corresponds to a single bit. For example, byte 320 includes a string of 8-one bits, and is thus treated (or read) by the receiver 97 as if it were a single bit "1". As an additional example, byte 323 includes a string of 8-zero bits, and is thus treated by the receiver 97 as if it were a single bit "0". As a result, the patient control unit 62 receives data at an equivalent data rate of 1024 BPS, which does not affect the hardware implementation of the pacemaker 10.

Figure 7:
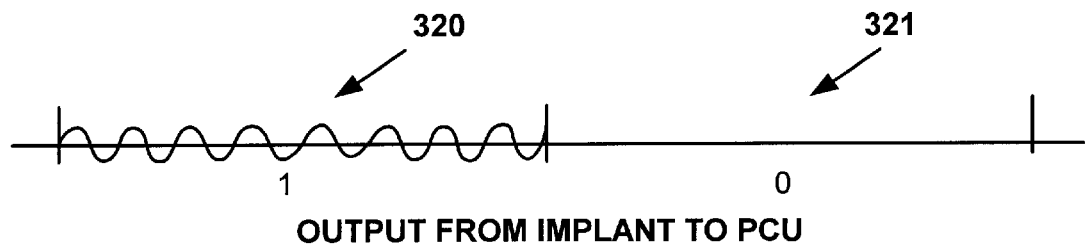
FIG. 7 depicts two signals representative of two bytes in a stream of data from the implantable device to the patient control unit of FIGS. 1 and 4.

FIG. 7 depicts two signals representative of two bytes "1" and "0" in a stream of data from the pacemaker 10 to the patient control unit 62, as received by the coil 96. The "1" byte 320 is represented by a sinusoidal waveform that may be used with the operation of the burst mode transmitter 72 of the pacemaker 10.

Figure 8:
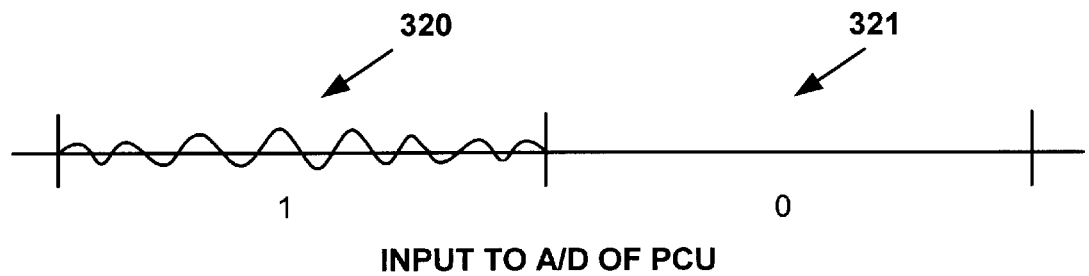
FIG. 8 depicts two signals representative of two bytes in a stream of data from the implantable device to the input of an analogue-to-digital (A/D) converter forming part of the patient control unit of FIGS. 1 and 4.

FIG. 8 depicts the signals of FIG. 7 after they have been processed by the band-pass filter 97 of the patient control unit 62.

The patient control unit 62 in general, will transmit only a few frames to "open the channel" of a particular pacemaker 10, after which it sends only one frame with a command. In the first part of this command frame, the patient control unit 62 transmits only 8 bits: 6 bits as a control word with a particular pattern being recognized by implant as a command from a patient control unit 62, and 2 bits to select between 4 different commands. The second part of this frame contains information from the pacemaker 10 at 1 Kpbs. The 6 bits from the pacemaker 10 provide the patient with 64 different combinations or possible commands, which is a sufficient number for the intended purpose.

In operation, when the patient activates the patient control unit 62, the DSP chip U2 reads a code or a program stored in the EPROM U1. In addition, the DSP chip U2 can be hardwired for booting the program stored in the EPROM U1. Thus, the EPROM U1 can be selected from a variety of inexpensive readily available EPROMs. The patient control unit 62 then sends a special identification code to the pacemaker 10, which recognizes such identification code and responds by transmitting data at a special mode as explained above, which represents a slower receive rate of the patient control unit 62.

It is therefore clear that due to the low reception transfer rate of 1 Kbps, the patient control unit 62 can be implemented inexpensively with minimal components. Though the reception transfer rate to the patient control unit 62 is lower than the transmission rate of 8 Kbps, this tradeoff is justified as the patient does not usually need significant information to be transferred from the pacemaker 10.

While FIGS. 7 and 8 illustrate each byte as being comprised of 8 identical bits, it should be clear that in other embodiments, each byte can be comprised of a different number of bits. Alternatively, each byte may include two or more strings of identical bits. As an example, byte 324 can consist of the following data bit sequence: "11110000", which can be read as a two-bit sequence: "10". As another example, byte 324 can consist of the following data bit sequence: "11001100", which can be read as a four-bit sequence: "1010". These examples illustrate the lower data transfer mode, where data received by the patient control unit 62 is transferred at less than the optimal transfer rate.

Moreover, while the higher transfer rate has been described as being implemented at an 8 Kbps transfer rate, it should be clear that a different (e.g. higher) rate can be used, as described in copending patent application, titled "High Speed Telemetry System Using Transmission Medium as a Component of a Telemetry Link," Ser. No. 09/415,480, filed Oct. 8, 1999, now U.S. Pat. No. 6,301,504, which is incorporated herein in its entirety.

While the invention described herein has been described with reference to particular embodiments of the patient control unit, modifications could be made thereto by those skilled in the art without departing from the spirit and scope of the invention.

What is claimed is:

1. A user control unit for communicating with an implantable device, comprising:

an input element for enabling the user to select one or more commands to be transmitted to the implantable device;

a transmitter for transmitting the one or more commands selected by means of the input element;

a receiver for receiving data from the implantable device; and a controller for establishing a bidirectional, asymmetric, dual-mode telemetry link to communicate with the implantable device;

wherein in a first mode, the transmitter transmits data to the implantable device at a first rate, and in a second mode, the receiver receives data from the implantable device at a second rate, and wherein the first rate is higher than the second rate;

wherein the first rate is approximately 8 Kbps; and wherein the second rate is approximately 1 Kbps.

2. A user control unit for communicating with an implantable device, comprising:

an input element for enabling the user to select one or more commands to be transmitted to the implantable device;

a transmitter for transmitting the one or more commands selected by means of the input element;

a receiver for receiving data from the implantable device; and a controller for establishing a bidirectional, asymmetric, dual-mode telemetry link to communicate with the implantable device;

wherein in a first mode, the transmitter transmits data to the implantable device at a first rate, and in a second mode, the receiver receives data from the implantable device at a second rate, and wherein the first rate is higher than the second rate;

wherein in the second mode, the implantable device transmits data as a sequence of bytes; and wherein each byte is comprised of a plurality of identical bits.

3. The user control unit according to claim 2, further including a status indicator for providing the user with a confirmation response from the implantable device.

4. The user control unit according to claim 3, wherein the status indicator provides a visual indication to the user.

5. The user control unit according to claim 3, wherein the status indicator provides an audible indication to the user.

6. The user control unit according to claim 2, further including a switch that sends the one or more commands to the implantable device.

7. The user control unit according to claim 6, wherein the input element is a two-position switch.

8. The user control unit according to claim 2, wherein the receiver includes a band-pass filter that receives signals from the implantable device for generating filtered signals.

9. The user control unit according to claim 8, further including an analogue to digital converter that digitizes the filtered signal before they are processed by the controller.

10. The user control unit according to claim 8, wherein the band-pass filter includes two second order band-pass filter circuits connected in series.

11. The user control unit according to claim 10, wherein the controller includes a latch that controls the operation of the two second order band-pass filter circuits;

wherein in the first mode the latch resets both filter circuits; and wherein, upon completion of the first mode, the latch activates the filter circuits sequentially.

12. The user control unit according to claim 8, wherein the band-pass filter receives signals from the implantable device at the first rate and generates filtered signals at the second rate.

13. The user control unit according to claim 2, wherein the controller includes:

a memory for storing an executable program; and a digital signal processing chip that executes the program.

14. The user control unit according to claim 2, wherein the first rate is an "n" bit multiple of the second rate.

15. A telemetry system, comprising:
a telemetry circuit contained at least in part within the implantable device; and
a user control unit including:
- an input element for enabling the user to select one or more commands to be transmitted to the telemetry circuit;
- a transmitter for transmitting the one or more commands selected by means of the input element;
- a receiver for receiving data from the telemetry circuit;
- a controller for establishing a bidirectional, asymmetric, dual-mode telemetry link to communicate with the telemetry circuit,
- wherein in a first mode, the transmitter transmits data to the telemetry circuit at a first rate, and in a second mode, the receiver receives data from the telemetry circuit at a second rate, wherein the first rate is higher than the second rate;
- wherein in the second mode, the telemetry circuit transmits data as a sequence of bytes; and
- wherein each byte is comprised of a plurality of identical bits.

16. The telemetry system according to claim 15, wherein the telemetry circuit includes a receiver and a transmitter.

17. The telemetry system according to claim 16, wherein the receiver of the user control unit includes a band-pass filter that receives signals from the transmitter of the telemetry circuit for generating filtered signals; and
wherein the receiver of the user control unit further includes an analogue to digital converter that digitizes the filtered signals before they are processed by the controller.

18. The telemetry system according to claim 15, wherein the first rate is approximately 8 Kbps; and
wherein the second rate is approximately 1 Kbps.

19. The telemetry system according to claim 15, wherein the user control unit further includes a status indicator for providing the user with a confirmation response from the telemetry circuit.

20. The user control unit according to claim 15, wherein the receiver includes a band-pass filter that receives signals from the implantable device at the first rate and generates filtered signals at the second rate.

21. The user control unit according to claim 15, wherein the first rate is an "n" bit multiple of the second rate.

22. A method for establishing communication between a user control unit and an implantable device, comprising:
- enabling a user to select one or more commands to be transmitted to the implantable device;
- transmitting the one or more commands selected by the user;
- receiving data from the implantable device;
- establishing a bidirectional, asymmetric, dual-mode telemetry link between the implantable device and the user control unit;
- wherein in a first mode, a transmitter transmits data to the implantable device at a first rate, and in a second mode, a receiver receives data from the implantable device at a second rate, and wherein the first rate is higher than the second rate; and
- wherein receiving at the second mode includes receiving data as a sequence of bytes, wherein each byte is comprised of a plurality of identical bits.

23. The method according to claim 22, wherein transmitting at the first rate includes transmitting at approximately 8 Kbps; and
wherein receiving at the second rate includes receiving at approximately 1 Kbps.

24. The method according to claim 22, further including providing the user with a confirmation response from the implantable device.

25. The method according to claim 22, wherein the receiving comprises:
- receiving encoded data from the implantable device at the first rate;
- band-pass filtering the encoded data so as to produce filtered data that can be decoded at the second rate.

26. A user control unit for communicating with an implantable device, comprising:
- a transmitter for transmitting one or more commands to the implantable device;
- a receiver for receiving data from the implantable device;
- a controller for establishing a bidirectional, asymmetric, dual-mode telemetry link to communicate with the implantable device;
- wherein in a first mode, the transmitter transmits data to the implantable device at a first rate, and in a second mode, the receiver receives data from the implantable device at a second rate, and wherein the first rate is higher than the second rate; and
- wherein the data received is encoded so that it can be transmitted at the first rate but interpreted by the receiver at the second rate.

27. A telemetry system for use with an implantable device, the telemetry system comprising:
- a patient operated telemetry module configured to transmit signals to the implantable device configured to receive signals from the implantable device using a low data transmission rate; and
- an internal telemetry module, located within the implantable device, configured to receive and transmit signals at a high data transmission rate, and further configured to encode a data signal so that it can be transmitted at the high data transmission rate and interpreted by the patient operated telemetry module at the low data transmission rate.

28. The telemetry system according to claim 27, wherein:
the patient operated telemetry module comprises a filter that filters the encoded data signal to produce filtered data signal that can be interpreted at the second rate.

29. The telemetry system according to claim 27, wherein the first rate is an "n" bit multiple of the second rate.

30. The telemetry system according to claim 29, wherein the ratio of the first rate to the second rate is at least one of 8:1, 4:1 or 2:1.

* * * * *